US012642916B2

(12) United States Patent
Bastian et al.

(10) Patent No.: US 12,642,916 B2
(45) Date of Patent: Jun. 2, 2026

(54) METHOD OF PROVIDING A PERSONAL DRUG INJECTION SYSTEM

(71) Applicant: EFX Medical Technologies Pty Ltd, Nedlands (AU)

(72) Inventors: Emily May Bastian, Dalkeith (AU); Samuel Luke Johnstone, Cambridge (GB); Heather Kathleen Jameson, Cambridge (GB); Kristien De Clercq, Cambridge (GB); Bradley Sawyer, London (GB)

(73) Assignee: EFX MEDICAL TECHNOLOGIES PTY LTD, Nedlands (AU)

( * ) Notice: Subject to any disclaimer, the term of this patent is extended or adjusted under 35 U.S.C. 154(b) by 0 days.

(21) Appl. No.: 18/914,004

(22) Filed: Oct. 11, 2024

(65) Prior Publication Data

US 2025/0229038 A1      Jul. 17, 2025

Related U.S. Application Data

(60) Provisional application No. 63/688,241, filed on Aug. 28, 2024.

(30) Foreign Application Priority Data

Jan. 12, 2024      (AU) ................................. 2024900090

(51) Int. Cl.
*A61M 5/32* (2006.01)
*A61M 5/315* (2006.01)
(52) U.S. Cl.
CPC ...... *A61M 5/3294* (2013.01); *A61M 5/31576* (2013.01); *A61M 5/31593* (2013.01)

(58) Field of Classification Search
CPC .... A61M 5/3294; A61M 5/2066; A61M 5/19; A61M 5/2033; A61M 2005/31508;
(Continued)

(56) References Cited

U.S. PATENT DOCUMENTS 6,656,147 B1      12/2003   Gertsek et al.
9,099,044 B2      8/2015    Kuo et al.
(Continued)

FOREIGN PATENT DOCUMENTS

WO      2022053948 A1      3/2022

*Primary Examiner* — Laura A Bouchelle
*Assistant Examiner* — Sarah Dympna Grasmeder
(74) *Attorney, Agent, or Firm* — Procopio, Cory, Hargreaves & Savitch LLP; Brent Johnson; Blake Winn

(57) ABSTRACT

A method of providing a personal drug injection system is disclosed. The method comprises determining at least one anthropometric characteristic from a person, and providing a plurality of types of personal drug injection systems. Each personal drug injection system of a personal drug injection system type is configured so as to fit with a part of the person's body that is intended to receive an injectable drug, and includes a drug injection location set that includes at least one defined drug injection location corresponding to a location of a drug injection site on the part of the person's body when the personal drug injection system is disposed on the part of the person's body. Each personal drug injection system type is associated with a defined range of anthropometric characteristics that is different to the defined range of anthropometric characteristics associated with the other personal drug injection system types.

28 Claims, 10 Drawing Sheets

(58) Field of Classification Search
CPC .. A61M 2005/2073; A61M 2005/3103; A61M
2005/3104; A61M 2005/3106
See application file for complete search history.

(56) References Cited

U.S. PATENT DOCUMENTS

| | | |
|---|---|---|
| 2005/0148935 A1 | 7/2005 | Dimitrova et al. |
| 2010/0179473 A1 | 7/2010 | Genosar |
| 2012/0245558 A1 | 9/2012 | Durack et al. |
| 2014/0039451 A1 | 2/2014 | Bangera et al. |
| 2017/0246393 A1 | 8/2017 | Genosar |
| 2017/0259013 A1 | 9/2017 | Boyden et al. |
| 2019/0231470 A1 | 8/2019 | Fink et al. |
| 2020/0093997 A1 | 3/2020 | Jandali et al. |
| 2020/0179618 A1 | 6/2020 | Jandali et al. |
| 2020/0324061 A1 | 10/2020 | Ament |
| 2022/0203033 A1* | 6/2022 | Cowe ................ A61M 5/31596 |

* cited by examiner

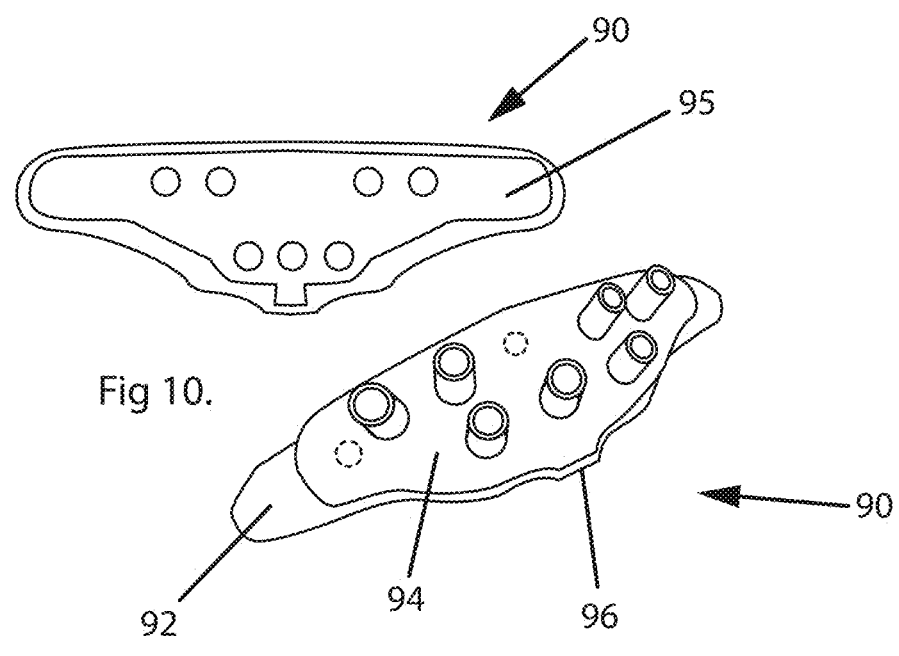
Fig 10.
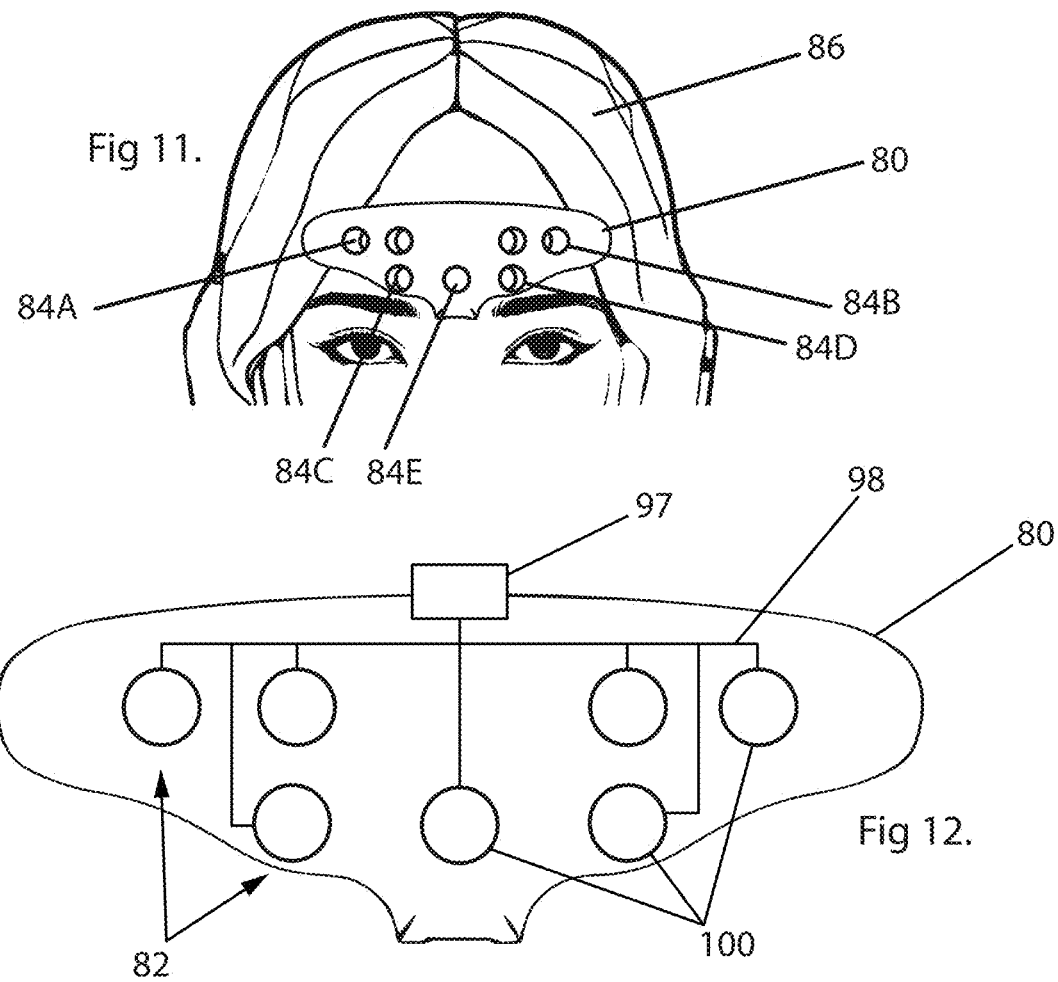
Fig 11.
Fig 12.

METHOD OF PROVIDING A PERSONAL DRUG INJECTION SYSTEM

FIELD

The present disclosure relates to a method of providing a personal drug injection system and to a personal drug injection system provided by the method.

BACKGROUND

For some treatment processes, it is necessary to inject a drug into body tissue at one or more particular locations. The injections are typically administered by a medical professional, or by a clinician under the guidance of a medical professional.

For example, some cosmetic treatment processes require injection of a neuromodulator, which might include botulinum toxin, at defined body locations, for example to treat glabellar lines, lateral canthal lines (crow's feet) and horizontal forehead lines.

It is also known that a neuromodulator, such as botulinum toxin, can be used to treat primary axillary hyperhidrosis (PAH) by injection into multiple defined sites in the hyperhidrotic area of each axilla.

It is also known that a neuromodulator, such as botulinum toxin, can be used to treat migraine by paralysing specific muscles of the head and neck to thereby prevent spasms that might cause a migraine to develop.

The migraine treatment process involves injection of a neuromodulator, typically botulinum toxin, into several defined injection sites on a person's face that correspond to locations in corrugator supercilii, procerus and frontalis muscles. Such a treatment process is commonly in accordance with an injection protocol conforming to the Phase II research Evaluating Migraine Prophylaxis Therapy (PREEMPT) study.

For some treatments that use botulinum toxin injections, it is typical for a person to receive repeated treatment injections at periodic intervals, such as every 2 to 4 months, because the effects of the toxin subside over time. Because of this, the person is conventionally required to visit a clinician or medical professional in order to receive the injections.

However, it is known that patient satisfaction with neuromodulator injections can vary because of variances between the injection locations selected during different visits. It is also cumbersome, time consuming, and typically less sterile for the person to be required to periodically visit the medical professional or clinician, particularly since the treatment process requires very little time to implement.

In order to provide a more repeatable injection pattern, a mask may be configured to fit with a part of a person's body, the mask defining appropriate locations for injection of a drug when the mask is worn by the person. The mask may be used by a clinician or by the person such that for example the person may self-administer the drug.

Each of US 2020/0093997 and US 2020/0179618 discloses a cover for placement over a portion of a body of a patient and injection of a drug, and U.S. Pat. No. 9,199,044 discloses a wearable device that includes needle access regions arranged in a treatment pattern.

However, each arrangement contemplated by US 2020/0093997, US 2020/0179618 and U.S. Pat. No. 9,199,044 is individually customised to a single user, and as a consequence the process for creating the mask is cumbersome and expensive to implement, and the associated business model involving individual ad hoc production of masks is not cost effective or practical.

With respect to the aforementioned masks, several disadvantages exist with the design, construction and technology involved, including:

1. Complexity and Cost of Customisation. The prior art bespoke solutions require complex, time-consuming processes for customisation, which are expensive and not scalable for mass production. The dependence of these devices on individualised customisation makes these solutions impractical for widespread commercial use, as the production costs are prohibitively high and the process is inefficient.

2. Limited Commercial Viability. The bespoke nature of the above-mentioned devices and their technology limits their commercial viability. Producing each mask to fit a specific user involves high costs and significant time investment, making it challenging to supply these products at a scale that would be economically feasible for a broader market. The reliance on custom fabrication processes hinders the ability to pre-produce masks in large quantities, leading to longer lead times and reduced availability.

3. Dependence on Medical Professionals. Some prior art solutions rely on a medical professional or a clinician to perform the injections using external syringes or methods. This dependency on medical professionals for each injection session reduces patient autonomy and convenience, as patients must visit healthcare providers for every treatment. Moreover, the need for clinician-administered injections increases the overall cost and complexity of the treatment process, making it less accessible for patients who might benefit from more frequent or regular treatments, or those that might not be able to access suitably qualified medical professionals or clinicians.

4. Inconvenience and Risk of Manual Reconstitution. Ensuring the proper storage and reconstitution of botulinum toxin is critical due to its sensitivity and short shelf-life post-reconstitution. Existing solutions often involve manual reconstitution steps that are cumbersome and increase the risk of contamination and handling errors. The reliance on external syringes and manual preparation adds to the complexity and inconvenience for patients and clinicians alike, reducing sterility, and further conflating the reliance on injection of the drug by clinicians in a healthcare setting.

Separately and in addition to the requirement to inject botulinum toxin at appropriate locations, it is also important to ensure that the toxin is stored and reconstituted appropriately. For example, it is known that botulinum toxin is easily denatured, typically has required cold chain handling, requires reconstitution at an appropriate dilution amount and has a limited shelf life once reconstituted.

In view of the preference to reconstitute botulinum toxin shortly prior to injection, injection devices m include 2 separately stored components of the toxin, and manual or pressurised fluid activated arrangements for causing the 2 components to come together and thereby form the botulinum toxin for injection.

However, such manual arrangements typically rely on a person to first determine the actions required to cause reconstitution to occur, then manually carry out the actions before injection can occur, and pressurised fluid-based arrangements are overcomplicated and expensive to implement.

It is therefore the object of this disclosure to introduce a novel method of providing a personal drug injection system that leverages automation while simultaneously avoiding reliance on clinicians for injection of the drug.

SUMMARY

The present disclosure describes a method that involves gathering data inputs for a sizing algorithm from a patient's face, then assigning one of several standard sizes of masks for application to the patient's face based on the data inputs. This approach contrasts sharply with the bespoke mask creation process, and offers a more cost-effective and commercially viable solution.

The lack of standardisation with other arrangements prevents the efficient assignment of masks for application to patients' faces based on a set of predetermined sizes. The individualised nature of the prior art processes necessitates a bespoke production process for each patient, which is both time-consuming and costly. This approach does not support the scalable and efficient distribution of masks, which is essential for widespread adoption and commercial success.

By utilising pre-manufactured masks available in standard sizes, the present method reduces production costs and improves commercial viability. The injection system associated with the method is designed for self-administration, allowing patients to perform their own injections without the need for a clinician, thereby enhancing convenience and reducing overall treatment costs. Additionally, the integration of in-situ drug delivery mechanisms within the masks simplifies the process and minimises the risk of contamination and handling errors.

Furthermore, the present method utilises a standardised set of masks and in some embodiments incorporates a machine learning feedback loop that allows for easy reassignment of new masks within the standard set. This method can accommodate changes in a patient's facial structure due to aging or other factors and can also adapt to patient-preferred outcomes. By continually refining the mask assignment process through machine learning, the present method ensures ongoing accuracy and patient satisfaction without the need for expensive and time-consuming customisation.

The present method overcomes significant prior art disadvantages by providing a standardised, cost-effective, and user-friendly solution for drug injection treatments. The method enhances patient autonomy, reduces treatment costs, and improves accessibility, making it a practical and scalable alternative for a wide range of medical and cosmetic applications.

The present disclosure provides a method of providing a personal drug injection system, the method comprising:
 determining at least one anthropometric characteristic from a person;
 providing a plurality of types of personal drug injection systems;
 wherein each personal drug injection system of a personal drug injection system type:
 is configured so as to fit with a part of the person's body that is intended to receive an injectable drug; and
 includes a drug injection location set that includes at least one defined drug injection location corresponding to a location of a drug injection site on the part of the person's body when the personal drug injection system is disposed on the part of the person's body; and
 wherein each personal drug injection system type is associated with a defined range of anthropometric characteristics that is different to the defined range of anthropometric characteristics associated with the other personal drug injection system types, and each personal drug injection system type has an associated drug injection location set that is different to the drug injection location set of the other personal drug injection system types;
 using the determined anthropometric characteristic and the defined ranges of anthropometric characteristics to select one of the personal drug injection system types from the plurality of personal drug injection system types; and
 providing the person with the selected personal drug injection system type.

The inventors have realised that a degree of tolerance exists in relation to the injection location of a drug into a patient muscle, and based on this a defined small number of personal drug injection system types may be mass produced, then one of the personal drug injection system types selected for each person based on the anthropometric characteristic(s) obtained from the person. This methodology has significant economic advantages as it avoids the need to individually produce a customised personal drug injection system for each person.

In an embodiment, the at least one anthropometric characteristic includes intercanthal separation distance.

In an embodiment, the at least one anthropometric characteristic includes distance between medial edges of the person's orbital ridges.

In an embodiment, the method comprises:
 determining at least one first anthropometric characteristic from the person;
 using the determined at least one first anthropometric characteristic to determine at least one second anthropometric characteristic; and
 using the determined at least one second anthropometric characteristic and the defined ranges of anthropometric characteristics to select one personal drug injection type from the plurality of personal drug injection types.

In an embodiment, the first anthropometric characteristic includes intercanthal separation distance.

In an embodiment, the second anthropometric characteristic includes distance between medial edges of the person's orbital ridges.

In an embodiment, the method comprises determining the at least one anthropometric characteristic by obtaining a 3D representation of at least a portion of a person's body. The 3D representation may be obtained using a LIDAR scanner and the method may comprise analysing the 3D representation to determine the at least one anthropometric characteristic.

In an embodiment, the method comprises determining the anthropometric characteristic by capturing an image of at least a portion of the person's body, and analysing the image to determine the at least one anthropometric characteristic.

In an embodiment, the method comprises determining the anthropometric characteristic by directly measuring the at least one anthropometric characteristic.

In an embodiment, the method comprises using machine learning to predict the at least one anthropometric characteristic and/or to select a personal drug injection system from the plurality of personal drug injection systems. The machine learning may include at least one convolutional neural network (CNN) trained using multiple body part representations and data indicative of at least one anthropometric characteristic associated with each body part representation. The CNN training may be supervised or unsupervised.

In an embodiment, at least one personal drug injection system is at least partially rigid.

In an embodiment, at least one personal drug injection system is at least partially flexible.

In an embodiment, at least one personal drug injection system comprises at least one fixed drug injection device.

In an embodiment, at least one personal drug injection system comprises at least one removable and attachable drug injection device.

In an embodiment, at least one personal drug injection system comprises at least one alignment component arranged to facilitate correct alignment of the personal drug injection system with the person's body part.

In an embodiment, the alignment component is arranged to engage with a defined feature of the person's body part such that the personal drug injection system is correctly aligned with the person's body part when the alignment component engages with the defined feature of the person's body part. The defined feature may be the underside of a person's orbital ridges.

In an embodiment, the alignment component comprises a visual feature of the personal drug injection system that is usable to align the personal drug injection system with the person's body part by visually aligning the visual feature with a defined feature of the person's body part. The visual feature may include a lower flat surface of the personal drug injection system and the defined feature may include an inner edge of an underside of the person's brow ridge.

In an embodiment, the part of the person's body may include at least a portion of a face of the person.

In an embodiment wherein the part of the person's body is a portion of a face of the person, the personal drug injection system includes a mask device that covers at least part of the person's face.

In an embodiment, the personal drug injection system may include a plurality of drug injection system modules connectable to each other.

In an embodiment, the drug injection modules include a forehead module and a crow's feet module attachable to the forehead treatment module to define an injection pattern for treatment of lateral canthal lines (crow's feet).

In an embodiment, the at least one drug includes a neuromodulator such as botulinum toxin or a synthetically derived analogue of botulinum toxin.

In an embodiment, the treatment process is a cosmetic treatment process for glabellar lines wherein a neuromodulator is injected into a person's corrugator muscles and procerus muscles. The at least one defined drug injection location may be a drug injection pattern determined according to an injection protocol defined by An FDA-approved botulinum toxin drug.

In an embodiment, the treatment process is a cosmetic treatment process for lateral canthal lines wherein a neuromodulator is injected into a person's lateral orbicularis oculi muscles. The at least one defined drug injection location may be a drug injection pattern determined according to an injection protocol defined by An FDA-approved botulinum toxin drug.

In an embodiment, the treatment process is a cosmetic treatment process for horizontal forehead lines wherein a neuromodulator is injected into a person's frontalis muscle. The at least one defined drug injection location may be a drug injection pattern determined according to an injection protocol defined by An FDA-approved botulinum toxin drug.

In an embodiment, the treatment process is a primary axillary hyperhidrosis (PAH) treatment process wherein a neuromodulator is injected intradermally. The at least one defined drug injection location may be a drug injection pattern determined according to an injection protocol defined by Allergan for injection of Botox®.

In an embodiment, the treatment process is a migraine treatment process wherein botulinum toxin is injected into a person's corrugator supercilii, procerus and frontalis muscles. The at least one defined drug injection location may be a drug injection pattern determined according to an injection protocol conforming to the Phase II research Evaluating Migraine Prophylaxis Therapy (PREEMPT) study.

In an embodiment, the plurality of personal drug injection systems includes 3 or 5 personal drug injection systems, each personal drug injection system associated with a different defined range of anthropometric characteristics.

The present disclosure also provides a personal drug injection system provided according to the first aspect of the present disclosure, the personal drug injection system configured to fit with a part of the person's body that is intended to receive an injectable drug, and the personal drug injection system including at least one defined drug injection location corresponding to a location of a drug injection site on the part of the person's body when the personal drug injection system is disposed on the part of the person's body.

In an embodiment, the personal drug injection system includes at least one fixed or removable drug injection device.

At least one drug injection device may include a first chamber containing a first substance and a second chamber containing a second substance, wherein fluid communication between the first and second chambers is prevented when a removable packaging member is attached to the drug injection device and fluid communication between the first and second chambers is enabled when the removable packaging member is removed from the drug injection device.

In an embodiment, at least one of the first and second chambers includes a plunger and a biasing device arranged to bias the plunger inwardly of the associated first or second chamber, wherein inward the movement of the plunger by the biasing device is prevented when the packaging member is attached to the drug injection device, and inward the movement of the plunger by the biasing device is enabled when the packaging member is removed from the drug injection device, such that removal of the packaging member causes the first and second substances to mix.

The present disclosure also provides a method of providing a personal drug injection system, the method (Method A) comprising:

using a physical instrument to obtain at least one anthropometric characteristic value by interaction between the physical instrument and a part of a person's body that is intended to receive an injectable drug;

providing at least 3 personal drug injection system types, wherein each personal drug injection system type is configured to fit with the part of the person's body, wherein the at least 3 personal drug injection system types include:

a first personal drug injection system type having a first drug injection location set that includes at least one defined drug injection location corresponding to a location of a drug injection site on the part of the person's body when the first personal drug injection system is disposed on the part of the person's body, the first personal drug injection system associated with a first defined range of anthropometric characteristic values;

a second personal drug injection system type having a second drug injection location set that includes at least one defined drug injection location corresponding to a location of a drug injection site on the part of the person's body when the second personal drug injection system is disposed on the part of the person's body, the second drug injection location set being different to the first drug injection location set of the first personal drug injection system type, and the second personal drug injection system type associated with a second defined range of anthropometric characteristic values that is different to the first defined range of anthropometric characteristic values; and a third personal drug injection system type having a third drug injection location set that includes at least one defined drug injection location corresponding to a location of a drug injection site on the part of the person's body when the third personal drug injection system is disposed on the part of the person's body, the third drug injection location set being different to the first and second drug injection location sets of the first and second personal drug injection system types, and the third personal drug injection system type associated with a third defined range of anthropometric characteristic values that is different to the first and second defined ranges of anthropometric characteristic value;

selecting one of the at least 3 personal drug injection system types by determining which of the first, second or third defined ranges of anthropometric characteristic values includes the anthropometric characteristic value obtained from the person; and providing the person with the selected personal drug injection system type.

The present disclosure also provides a method of administering a neuromodulator drug to a human patient, comprising:

positioning the selected personal drug injection system type of Method A on a face of the human patient at a defined location on the person's face, wherein the drug injection location set of the personal drug injection system type corresponds to a cosmetic treatment process for glabellar lines that includes injection of the neuromodulator into the human patient's corrugator muscles and procerus muscles; and injecting the neuromodulator into the human patient's corrugator muscles and procerus muscles using injection devices disposed at the drug injection site locations associated with the drug injection location set.

The present disclosure also provides a method of administering a neuromodulator drug to a human patient, comprising:

positioning the selected personal drug injection system type of Method A on a face of the human patient at a defined location on the person's face, wherein the drug injection location set of the personal drug injection system type corresponds to a cosmetic treatment process for lateral canthal lines that includes injection of the neuromodulator into the human patient's lateral orbicularis oculi muscles; and injecting the neuromodulator into the human patient's lateral orbicularis oculi muscles using injection devices disposed at the drug injection site locations associated with the drug injection location set.

The present disclosure also provides a method of administering a neuromodulator drug to a human patient, comprising:

positioning the selected personal drug injection system type of Method A on a face of the human patient at a defined location on the person's face, wherein the drug injection location set of the personal drug injection system type corresponds to a cosmetic treatment process for horizontal forehead lines that includes injection of the neuromodulator into the human patient's frontalis muscle; and injecting the neuromodulator into the human patient's frontalis muscle using injection devices disposed at the drug injection site locations associated with the drug injection location set.

The present disclosure also provides a method of administering a neuromodulator drug to a human patient, comprising:

positioning the selected personal drug injection system type of Method A on a face of the human patient at a defined location on the person's face, wherein the drug injection location set of the personal drug injection system type corresponds to a primary axillary hyperhidrosis (PAH) treatment process that includes injection of the neuromodulator intradermally; and injecting the neuromodulator intradermally into the human patient using injection devices disposed at the drug injection site locations associated with the drug injection location set.

The present disclosure also provides a method of administering a neuromodulator drug to a human patient, comprising:

positioning the selected personal drug injection system type of Method A on a face of the human patient at a defined location on the person's face, wherein the drug injection location set of the personal drug injection system type corresponds to a migraine treatment process wherein botulinum toxin is injected into a person's corrugator supercilii, procerus and frontalis muscles; and injecting the neuromodulator into the person's corrugator supercilii, procerus and frontalis muscles using injection devices disposed at the drug injection site locations associated with the drug injection location set.

Some embodiments include a selection set, comprising 3 to 5 different personal drug injection system types, wherein each personal drug injection system type is configured to fit with the part of the person's body, wherein the selection set comprises:

a first personal drug injection system type having a first drug injection location set that includes at least one defined drug injection location corresponding to a location of a drug injection site on the part of the person's body when the first personal drug injection system is disposed on the part of the person's body, the first personal drug injection system associated with a first defined range of anthropometric characteristic values;

a second personal drug injection system type having a second drug injection location set that includes at least one defined drug injection location corresponding to a location of a drug injection site on the part of the person's body when the second personal drug injection system is disposed on the part of the person's body, the second drug injection location set being different from the first drug injection location set of the first personal drug injection system type, and the second personal drug injection system type associated with a second defined range of anthropometric characteristic values that is different to the first defined range of anthropometric characteristic values; and a third personal drug injection system type having a third drug injection location set that includes at least one defined drug injection location corresponding to a location of a drug injection site on the part of the person's body when the third personal drug injection system is disposed on the part of the person's body, the third drug injection location set being different from both the first drug injection location set of the first personal drug injection system type and the second drug injection location set of the second personal drug injection system type, and the third personal drug injection system type is associated with a third defined range of anthropometric characteristic values that is different from both the first defined range of anthropometric characteristic values and the second defined range of anthropometric characteristic values.

BRIEF DESCRIPTION OF THE DRAWINGS

The present methods, devices, and related embodiments will now be described, by way of example only, with reference to the accompanying drawings, in which:

FIG. 10 is a representation of an example substantially flexible personal drug injection system;

FIG. 11 is a diagrammatic representation of the example personal drug injection system shown in FIG. 8 when the personal drug injection system is disposed on a person's face;

FIG. 12 is diagrammatic representation of an example arrangement for distributing a drug to multiple drug injection locations in an example personal drug injection system;

DESCRIPTION OF AN EMBODIMENT

Figure 1:
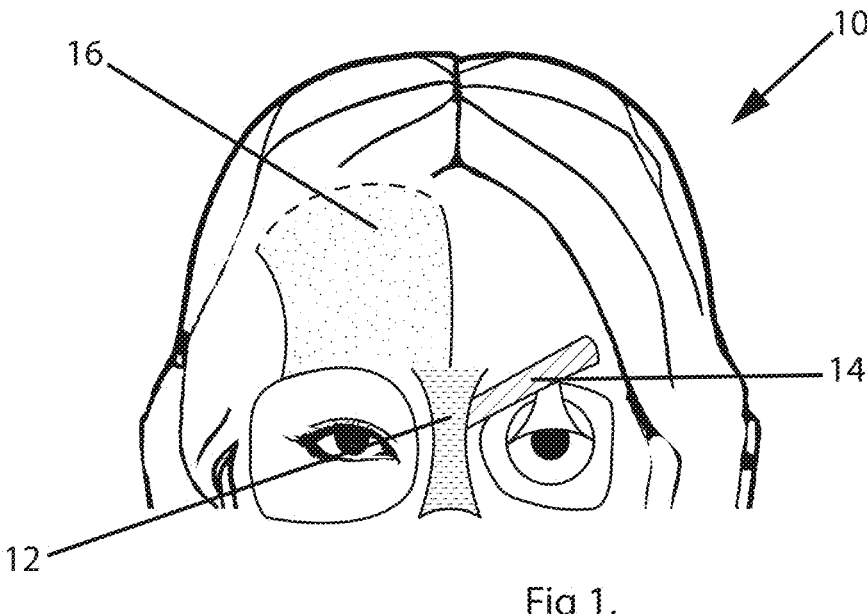
FIG. 1 is a diagrammatic representation of a portion of a human head showing relevant muscles associated with a defined part of the person's body that is intended to receive an injectable drug as part of an example treatment process.

The present disclosure relates to a method of providing a personal drug injection system to a person, the personal drug injection system of a type configured to deliver a drug to one or more defined locations on a person's body according to a defined treatment process by providing on the personal drug injection system at least one defined drug injection location corresponding to a location of a drug injection site on a body part when the personal drug injection system is disposed at a defined location on the body part.

For some treatment processes, a drug may be injected into body tissue at one or more particular locations defined by the treatment process. For example, a neuromodulator, such as botulinum toxin, injections can be used to treat migraine by paralysing specific muscles of the head and neck to thereby prevent spasms that might cause a migraine to develop, and injection of a neuromodulator can be used in a cosmetic treatment, for example to treat glabellar lines, lateral canthal lines (crow's feet) and horizontal forehead lines by paralysing specific muscles of the face to prevent movement that would result in these cosmetic effects.

At present, it is common for a person to receive botulinum toxin injection treatment by periodically visiting a medical professional or clinician, for example every 12 weeks.

The migraine treatment process involves injection of botulinum toxin into several defined injection sites on a person's face that correspond to locations in corrugator supercilii, procerus and frontalis muscles. Such a treatment process may be in accordance with an injection protocol conforming to the Phase II research Evaluating Migraine Prophylaxis Therapy (PREEMPT) study developed by Blumenfeld.

Since botulinum toxin is a toxic substance to humans, great care may be taken to ensure that the toxin is delivered to the correct locations, and for this reason botulinum toxin injections have typically been administered only by medical professionals or similarly trained and supervised clinicians.

Notwithstanding the risks associated with injection of botulinum toxin, the present inventors have realised that a degree of tolerance exists to the location of the injection sites in the relevant muscles to the extent that the desired treatment effect can be achieved even though the injection location may vary, so long as the relevant muscles have received a drug injection. The consequence of this is that it is not essential to receive injections solely by a medical professional, and it is feasible to implement an arrangement whereby injections are self-administered by a person. The practical degree of tolerance to the location of the injection sites also negates the need for an individual custom drug injection template that defines drug injection locations specific to each person receiving the treatment, and instead only a relatively small number of drug injection templates are required to cater for differing locations of corrugator supercilii, procerus and frontalis muscles.

The effect of this realisation is significant since it enables an efficient, primarily safe, cost-effective drug injection pattern-based treatment process to be implemented wherein a drug injection system with the most suitable drug injection pattern is selected for a person from a small set of drug injection systems based on one or more anthropometric characteristics obtained from the person. And importantly, since only a small number of different drug injection systems are provided, an arrangement for safe self-injection by a person becomes practically possible because the drug injection systems can be pre-manufactured and an appropriate injection system matched and provided to a person simply based on one or more anthropometric measurements obtained from the person.

In an example, 3 drug injection systems with different drug injection patterns are provided and one of the drug injection systems is selected using one or more anthropometric characteristic obtained automatically or manually from the person. However, it will be understood that other numbers of drug injection systems may be provided, such as 5.

For example, in the above example migraine treatment process according to the PREEMPT study, the anthropometric characteristic is orbital ridge medial edge separation that is estimated by determining the person's intercanthal separation distance.

However, it will be understood that any suitable anthropometric characteristic is envisaged, the important aspect being that the anthropometric characteristic is obtainable automatically or manually from a patient, and in the relevant treatment the drug injection locations are dependent on the obtained anthropometric characteristic.

It will also be understood that while the present examples relate to a migraine treatment process by administering a neuromodulator such as botulinum toxin according to the PREEMPT protocol, the present method is applicable to any treatment process that may involve injection of a drug at one or more defined locations and wherein a degree of tolerance exists in relation to the injection location. For example, the present method is applicable to treatment of conditions associated with overactive muscle movement, including cerebral palsy, post-stroke spasticity, post-spinal cord injury spasticity, and spasms of the head and neck; and to provide cosmetic treatments, for example to reduce facial wrinkles including frown lines, forehead wrinkles and crow's feet.

FIG. 1 shows a representation of a portion of a human head showing the muscles to be injected with botulinum toxin according to the PREEMPT study. The relevant muscles include a procerus muscle 12, a pair of corrugator supercilii muscles 14 and a pair of frontalis muscles 16.

Figure 2:
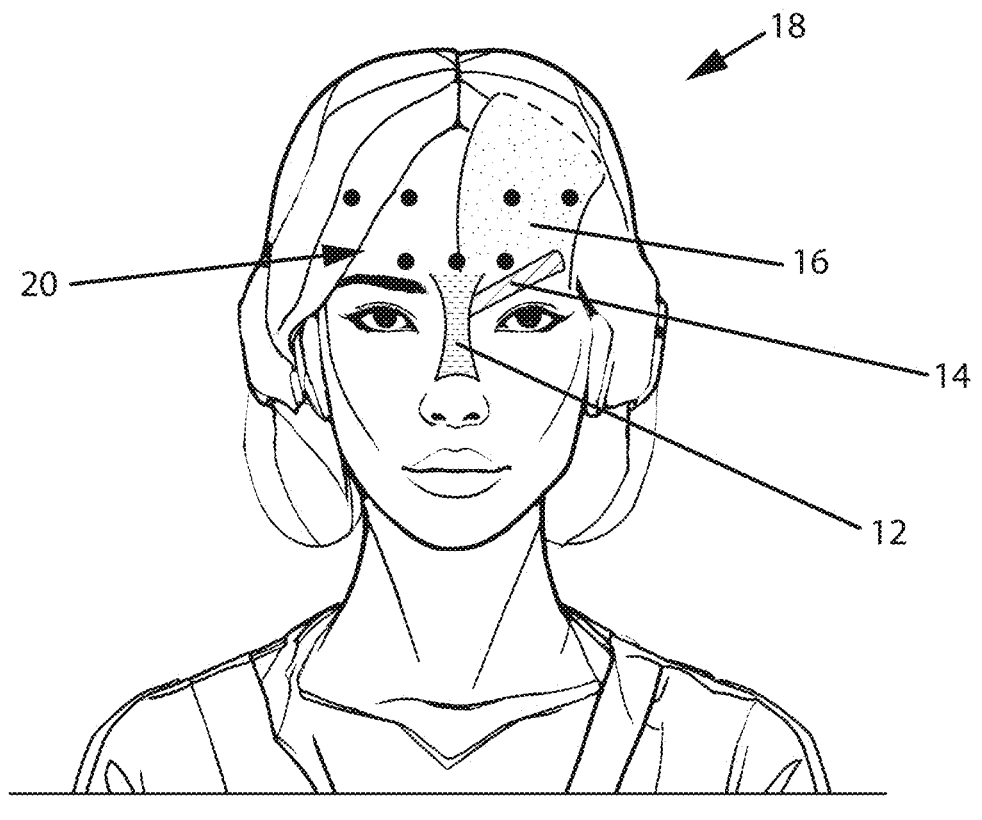
FIG. 2 is a diagrammatic representation of a human head showing an injection pattern associated with an example treatment process.
Figure 3:
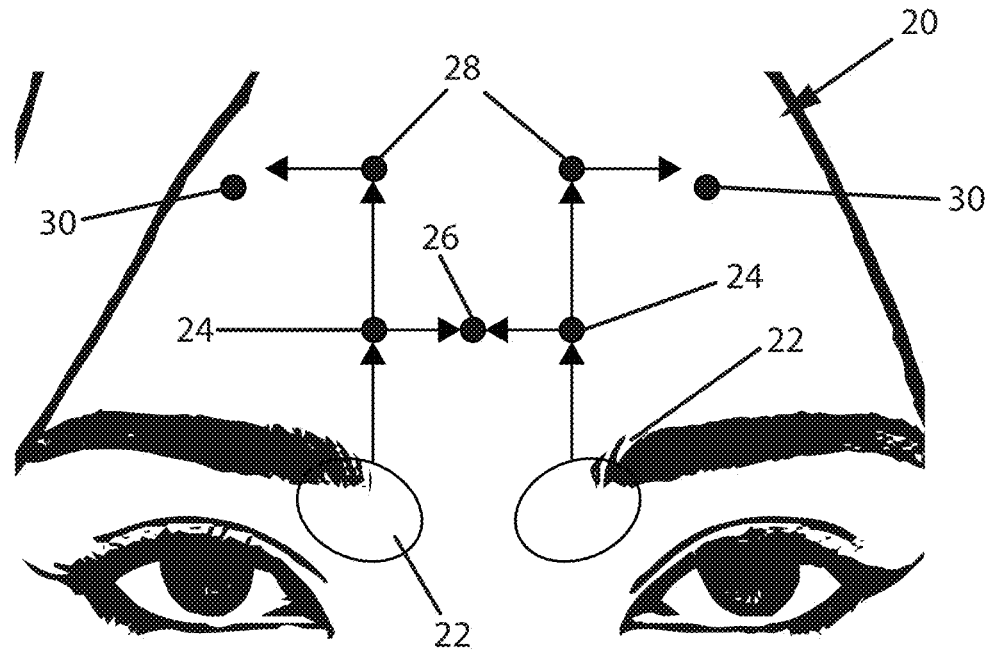
FIG. 3 is a representation of an example process for determining injection sites according to a defined injection pattern associated with an example treatment process.
Figure 4:
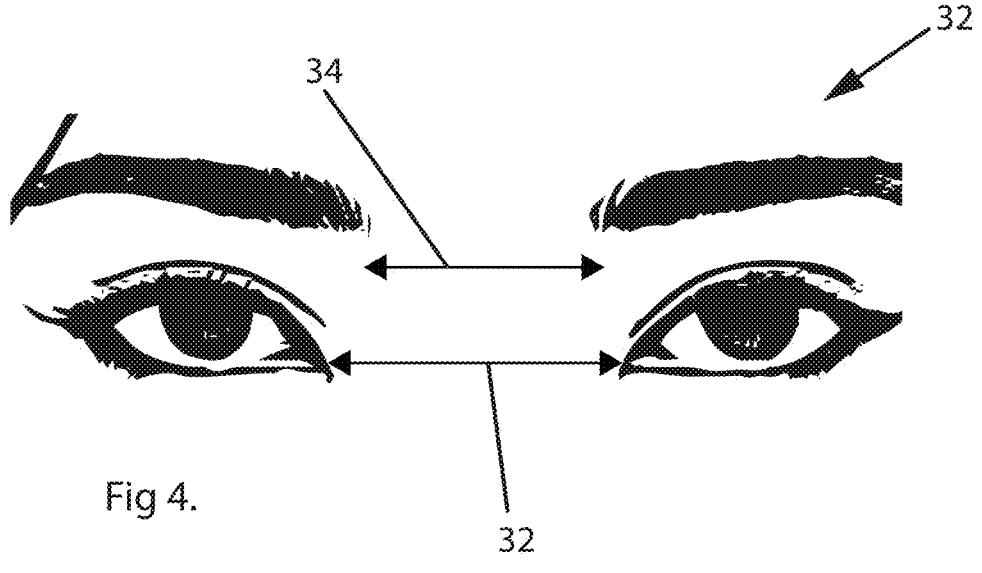
FIG. 4 is a representation of an example anthropometric characteristic associated with a person that is used to determine an injection pattern associated with an example treatment process and select a personal drug injection system from a plurality of personal drug injection systems.

An example human head 18 illustrating an example pattern 20 for injection of botulinum toxin is shown more in FIG. 2, and a process for determining the injection sites of the injection pattern 20 according to a PREEMPT protocol is illustrated in FIGS. 3 and 4.

In the present treatment example according to the PREEMPT study, an anthropometric characteristic, in this example orbital ridge medial edge separation that is estimated by first determining intercanthal separation 32, is determined either automatically or by direct measurement of the intercanthal separation. The intercanthal separation measurement corresponds to the distance between innermost locations of a person's eyes and the orbital ridge medial edge separation 34 is a distance between medial edges of the person's orbital ridges. The locations of the medial edges of the orbital ridges constitute anthropometric locations 22 on the person's face, the anthropometric locations 22 being used according to the PREEMPT protocol to identify first injection sites of an injection pattern.

It is known that in a person the distance between the medial edges of a person's orbital ridges is typically between 0 to 5 mm less than the intercanthal separation of the person, and in the present embodiment it has been assumed that the separation between orbital ridge medial edges is 5 mm less than the relevant intercanthal separation and the lateral location of each anthropometric location 22 is therefore estimated to be 2.5 mm inwardly of the medial canthus.

As shown in FIG. 3, according to the PREEMPT protocol, the following injection pattern is defined:

a pair of first injection sites 24 are defined with reference to the determined anthropometric locations 22, in this example such that each first injection site 24 is disposed at a location 15 mm vertically above an anthropometric location 22 corresponding to the expected location of the person's corrugator muscle;

a second injection site 26 is defined with reference to the first injection sites 24, in this example at a location centrally of a virtual line connecting the pair of first injection sites 24 corresponding to the expected location of the person's procerus muscle;

a pair of third injection sites 28 are defined with reference to the second injection sites 26, in this example such that each third injection site 28 is disposed at a location 15 mm vertically above a first injection site 24 corresponding to the expected location of the person's medial frontalis muscle; and a pair of fourth injection sites 30 are defined with reference to the third injection sites 28, in this example such that each fourth injection site 30 is disposed at a location 15 mm horizontally outwardly of a third injection site 28 corresponding to the expected location of the person's lateral frontalis muscle.

However, it will be understood that any injection pattern suitable for the treatment process is envisaged including any approved cosmetic protocol.

The intercanthal separation distance varies between people and consequently the distance between the corrugator supercilii muscles also varies.

It will be understood that the locations of the injection sites in the injection pattern is dependent on the locations of the anthropometric locations 22 and the separation distance between the anthropometric locations 22 therefore varies as the intercanthal distance varies. In turn, the distance between left side first 24, second 26, third 28 and fourth 30 injection sites and right side first 24, second 26, third 28 and fourth 30 injection sites varies based on varying intercanthal separation distance.

Figure 5:
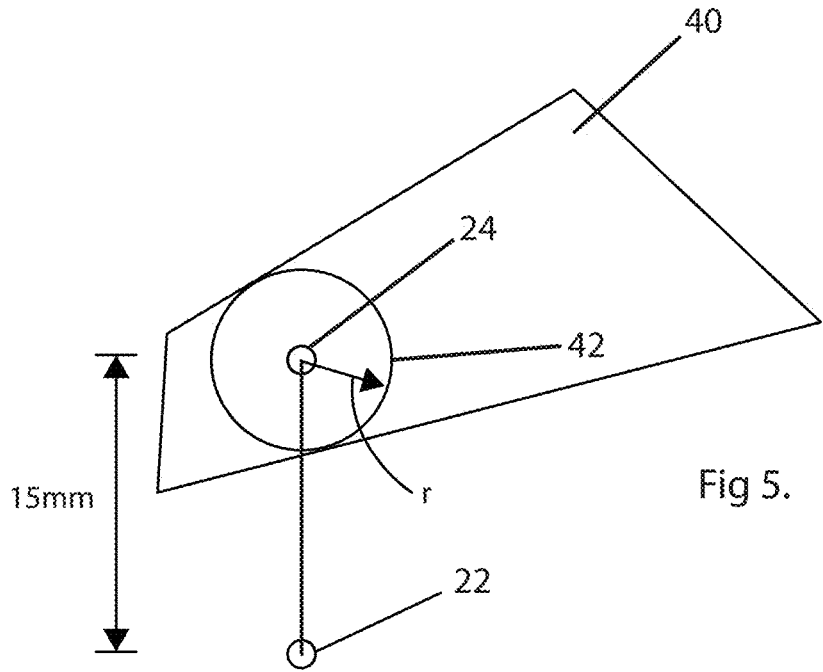
FIG. 5 shows a diagrammatic representation of a person's corrugator supercilii muscle that is intended to receive an injectable drug in an example treatment process.

FIG. 5 shows a diagrammatic representation of a person's left corrugator supercilii muscle 40 that extends generally diagonally above the left eye. In the present example, the corrugator supercilii muscle 40 receives an injection at a first injection site 24 determined based on an identified anthropometric location 22 corresponding to an orbital ridge edge.

The present inventors have realised that the present treatment process according to the PREEMPT clinical program produces satisfactory results in relation to the corrugator muscle 40 so long as an injection is received into the corrugator muscle 40. For the present example wherein a first injection is intended to be disposed at a first injection site 24 located 15 mm above an identified anthropometric location 22, for an average corrugator muscle 40 this corresponds to a tolerance of about 5.75 mm, represented by the tolerance circle 42 in FIG. 5 of radius r=5.75 mm. With this realisation, the inventors have concluded that a range of injection patterns with a range of separation distances between left and right injection sites will provide safe, cosmetically satisfactory treatment results for each person, and it is not necessary to produce specific individually customised drug injection systems with individually defined injection patterns.

In the present example, since the treatment process involves drug injections to a person at locations adjacent and above the person's eyes, the drug injection system that defines the drug injection pattern includes a mask device configured to define an injection pattern when the mask device is disposed on the person's face at a defined location relative to the person's face. The mask device may be disposed at a defined location by engaging with one or more facial features, such as the medial edges of the orbital ridges or by visually aligning with one or more facial features, for example by including one or more alignment features or alignment markers on the mask device. Correct alignment of the mask device with a person's facial features is important because the mask device defines a suitable injection pattern for the person and correct injection by virtue of the injection pattern is dependent on correct alignment of the mask with the person's corrugator muscle 40.

Figure 6:
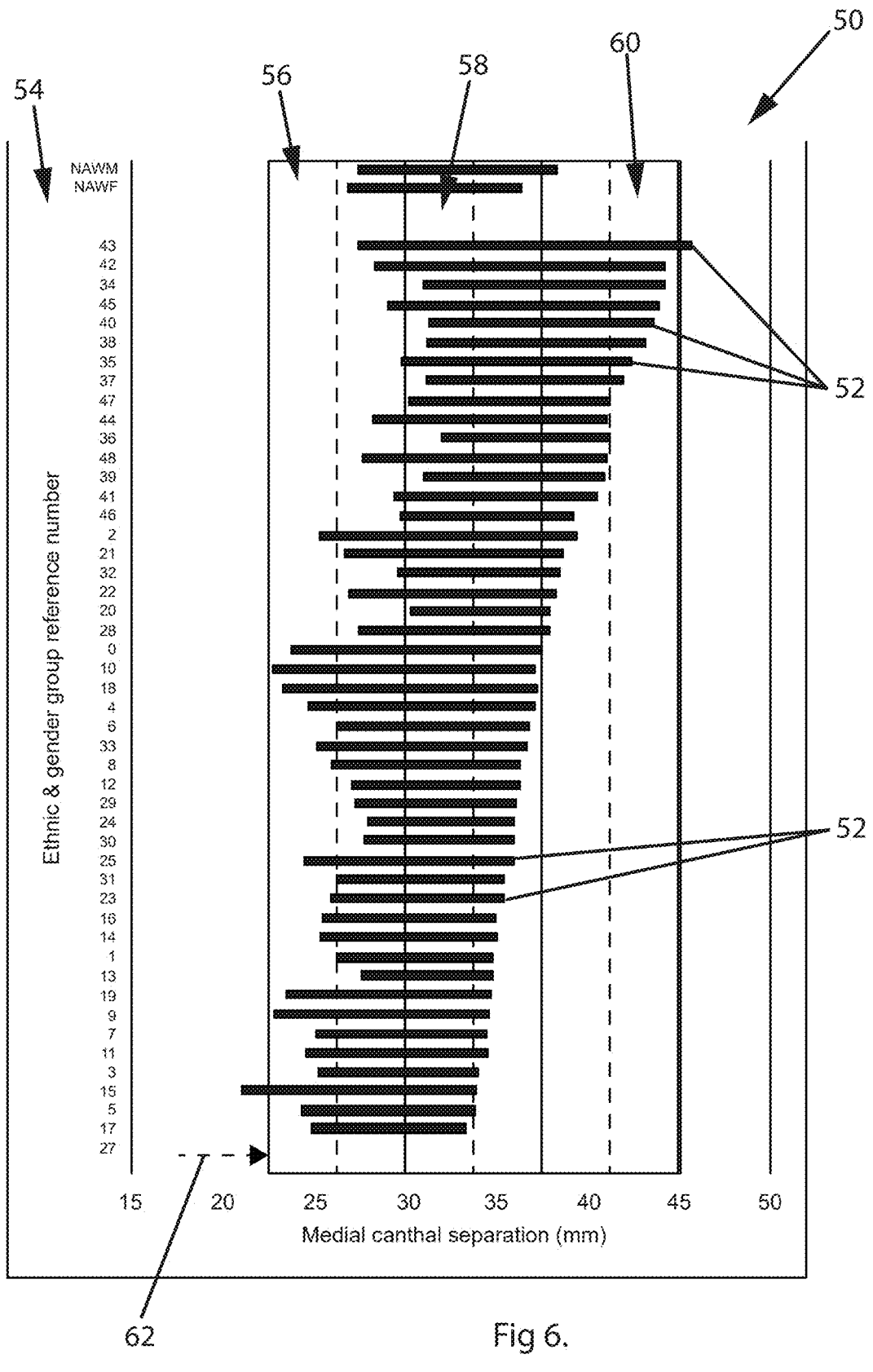
FIG. 6 shows example anthropometric characteristics for several ethnic and gender groups and example anthropometric characteristic ranges in an embodiment that includes 3 anthropometric characteristic ranges.

Referring to FIG. 6, a mask device chart 50 shows example anthropometric characteristics 52, in this example intercanthal separation, for several ethnic and gender groups 54. The mask device chart 50 also shows multiple, in this example 3, defined anthropometric characteristic ranges defined as 'small' 56, 'medium' 58 and 'large' 60, each range having a respective median value line 57, 59 and 61. In the present example, the small anthropometric characteristic range is between 22.5 mm and 30 mm with a median of 26.25 mm, the medium anthropometric characteristic range is between 30 mm and 37 mm with a median of 33.75 mm, and the large anthropometric characteristic range is between 37.5 mm and 45 mm with a median of 41.25 m.

Based on the 3 anthropometric characteristic ranges defined in FIG. 6, 3 drug injection systems, in this example in the form of 3 mask devices, are produced, each of which defines a set of injection locations corresponding to an injection pattern that is suitable for a range of people that fall into one of the 3 defined ranges of intercanthal separation. As such, multiple, in this example 3, mask types are produced with each mask type associated with a defined range of intercanthal separation and associated with a different set of injection locations.

The anthropometric characteristics 52 shown in FIG. 6 are based on orbital ridge separation distances with 5 mm added to each orbital ridge separation distance to estimate the corresponding intercanthal distance. This was done so that intercanthal distance is used as the anthropomorphic characteristic to determine selection of mask device type rather than orbital ridge separation distance, because intercanthal distance is easier to determine from a person than orbital ridge separation distance.

Using the categorisations defined in the mask device chart 50, a suitable mask device type for a person can be selected based on the intercanthal distance obtained from the person.

Figure 7:
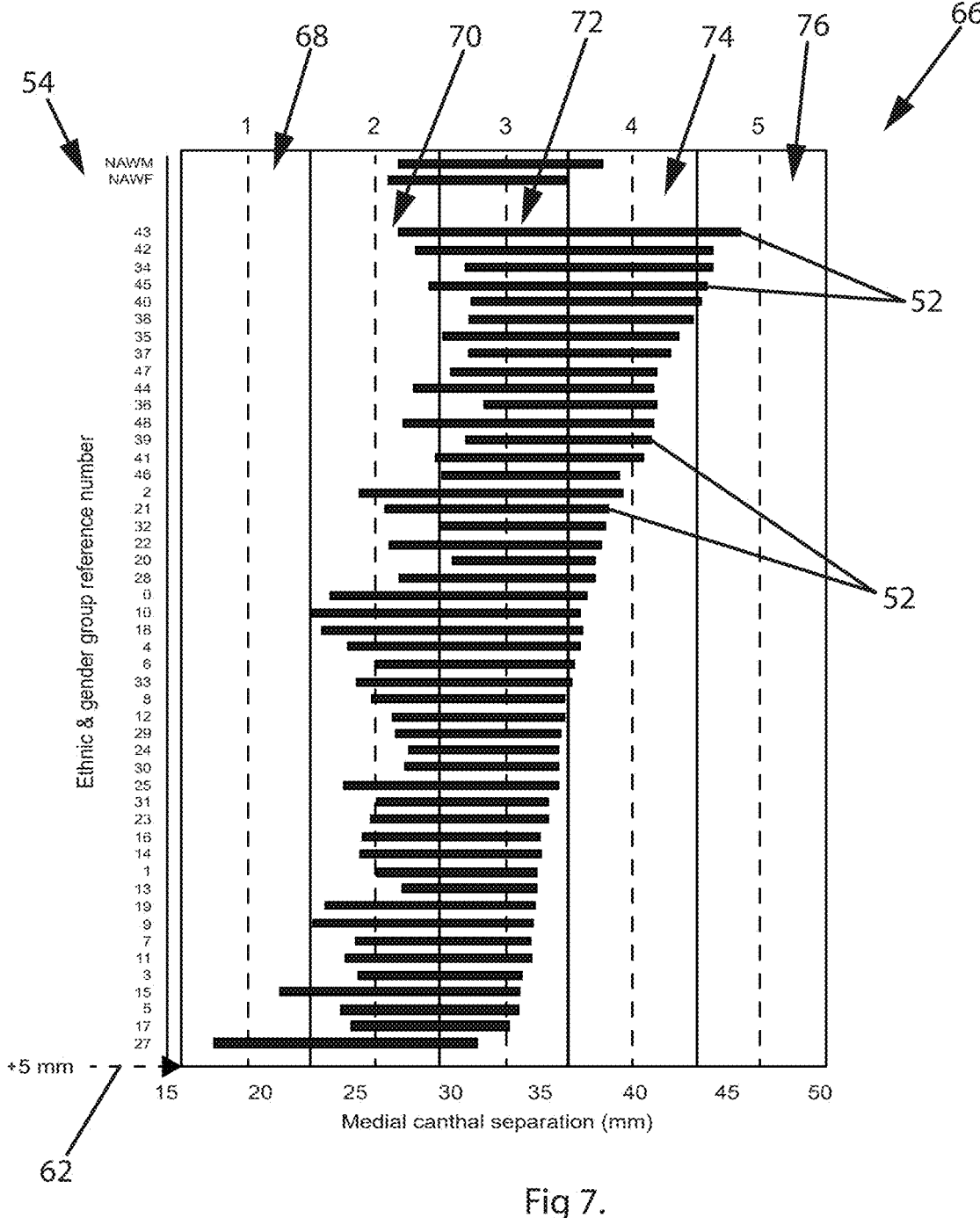
FIG. 7 shows example anthropometric characteristics for several ethnic and gender groups and example anthropometric characteristic ranges in an embodiment that includes 5 anthropometric characteristic ranges.

While FIG. 6 illustrates 3 anthropometric characteristic ranges that are used to categorise people into one of 3 mask device size categories based on determined intercanthal separation distance, it will be understood that any suitable number of anthropometric characteristic ranges and corresponding number of different mask device sizes are envisaged. For example, as shown in FIG. 7, a mask device chart 66 shows example anthropometric characteristics 52, in this example intercanthal separation, for several ethnic and gender groups 54, and 5 defined anthropometric characteristic ranges 68, 70, 72, 74, 76, 78 for patient intercanthal separation distances.

In the 5 range example, a first anthropometric characteristic range 68 is between 15.5 mm and 22.5 mm with a median of 29 mm, a second anthropometric characteristic range 70 is between 22.5 mm and 29.5 mm with a median of 26 mm, a third anthropometric characteristic range 72 is between 29.5 mm and 36.5 mm with a median of 33 mm, a fourth anthropometric characteristic range 74 is between 36.5 mm and 43.5 mm with a median of 39 mm, and a fifth anthropometric characteristic range 76 is between 43.5 mm and 49.5 mm with a median of 47 mm.

The anthropometric characteristic that is used to select a drug injection mask device, and therefore a suitable injection pattern, from a plurality of drug injection mask devices, may be determined in any suitable way, including by use of a physical instrument, such as a measuring device (e.g., a ruler, measuring tape, calipers, an optical device, etc.).

For example, the anthropometric characteristic may be determined automatically by obtaining a 3D representation of at least a portion of a person's face, for example using a LIDAR scanner that may be associated with a smartphone, and using a suitable software application implemented on the smartphone and arranged to determine an estimated intercanthal distance based on the LIDAR facial representation.

In a further example, the anthropometric characteristic is based on a photographic representation of at least a portion of the person's face, for example that is analysed using a suitable software application, such as implemented on a smartphone, to determine an estimated intercanthal distance based on any suitable identifiable facial features such as relative locations of facial features, relative sizes of facial features, and so on.

In a further example, the anthropometric characteristic is determined by direct measurement of the anthropometric characteristic, for example using a ruler or measuring tool.

In a further example, the anthropometric characteristic may be predicted using machine learning, for example using a convolutional neural network (CNN) that is trained using multiple facial representations, such as photographs, and ground truth data indicative of an anthropometric characteristic associated with each facial representation. The CNN training may be supervised wherein one or more anthropometric characteristic such as orbital ridge edges are marked on the facial representations or unsupervised wherein anthropometric characteristics are not marked on the facial representations. During use, a person may obtain a representation of the person's face, for example by taking a photograph using a smartphone, and the facial representation provided as an input to the neural network, which produces an output that predicts the most suitable mask device for the person. The machine learning may also be trained to select an appropriate mask device based on the obtained or predicted anthropometric characteristic, and a feedback look may be provided wherein the mask selection carried out by the machine learning may be modified based on user feedback in relation to mask performance.

In the above example, the personal drug injection system is configured to fit with a portion of a person's face such that an injection pattern is defined for treatment of migraine. In a variation, the personal drug injection system may be arranged such that one or more personal drug injection modules are attachable to each other to define a desired configuration for a personal drug injection system associated with a particular treatment and the relevant drug injection pattern for the treatment. For example, a crow's feet module may be attachable to a forehead treatment module to define an injection pattern for treatment of lateral canthal lines (crow's feet).

While the above specific example relates to a migraine treatment process by administering a neuromodulator according to the PREEMPT protocol, other treatment processes are envisaged.

For example, the treatment process may be a cosmetic treatment process for glabellar lines wherein a neuromodulator is injected into a person's corrugator muscles and procerus muscles. The applicable injection pattern may be in accordance with any suitable injection protocol, for example determined according to an injection protocol defined by An FDA-approved botulinum toxin drug.

In a further example, the treatment process is a cosmetic treatment process for lateral canthal lines wherein a neuromodulator is injected into a person's lateral orbicularis oculi muscles. The applicable injection pattern may be in accordance with any suitable injection protocol, for example determined according to an injection protocol defined by An FDA-approved botulinum toxin drug.

In a further example, the treatment process is a cosmetic treatment process for horizontal forehead lines wherein a neuromodulator is injected into a person's frontalis muscle. The applicable injection pattern may be in accordance with any suitable injection protocol, for example determined according to an injection protocol defined by An FDA-approved botulinum toxin drug.

In a further example, the treatment process is a primary axillary hyperhidrosis (PAH) treatment process wherein a neuromodulator is injected intradermally. The applicable injection pattern may be in accordance with any suitable injection protocol, for example determined according to an injection protocol defined by Allergan for injection of Botox®.

Figure 8:
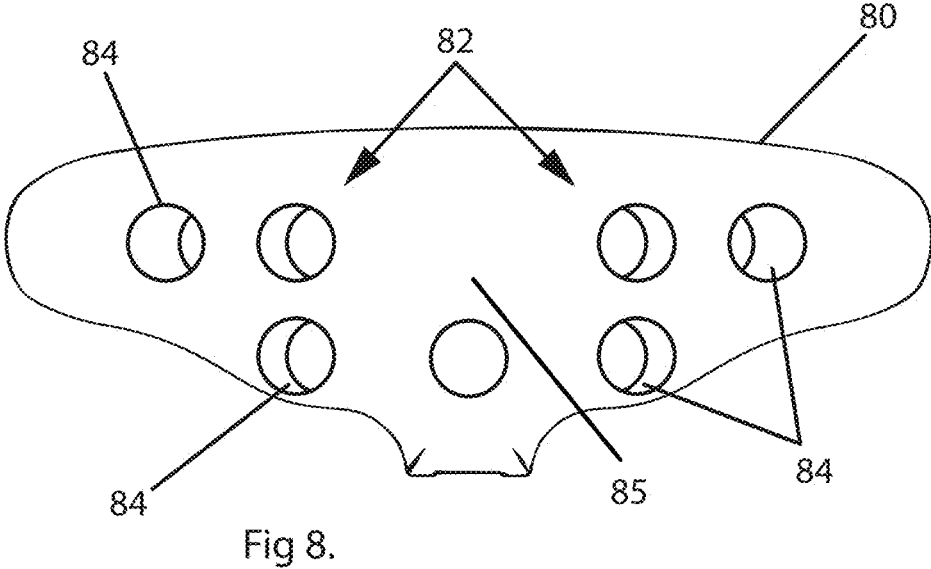
FIG. 8 is a diagrammatic representation of an example personal drug injection system for use in an example treatment process associated with injection of a drug to defined facial locations.

Referring to FIG. 8, an example drug injection system in the form of a mask device 80 is shown. The mask device 80 may be flexible, rigid or partly flexible and partly rigid, the important aspect being that the mask device is configured to define a set of injection locations associated with a drug injection pattern suitable for a treatment process and appropriately sized for the person when the drug injection mask is disposed at a defined location on a part of the person's body, in this example the person's face. The drug injection mask 80 may include physical components that facilitate alignment of the mask 80 with the person's face by engaging with features of the person's face, such as the orbital ridges, and/or alignment features that are used by a person to visually align the mask with the person's face at the correct location.

As shown in FIG. 8, the example mask 80 includes a defined pattern 82 of injection locations 84 with each injection location 84 defining a location for injection of a drug according to a treatment process.

In any injection device, a mask may include a substrate, e.g., substrate 85, which support the injection locations, or in which the injection locations, e.g., injection locations 84, are embedded or disposed. In some embodiments, one or more, or all of the injection locations may have an injector integrated into the substrate. One or more, or all of the injectors may contain a drug.

Each injection location may include a drug injection device or may be configured to receive a suitable drug injection device and for example engage with a drug injection device so that the drug injection device is retained relative to the mask 80.

Figure 13:
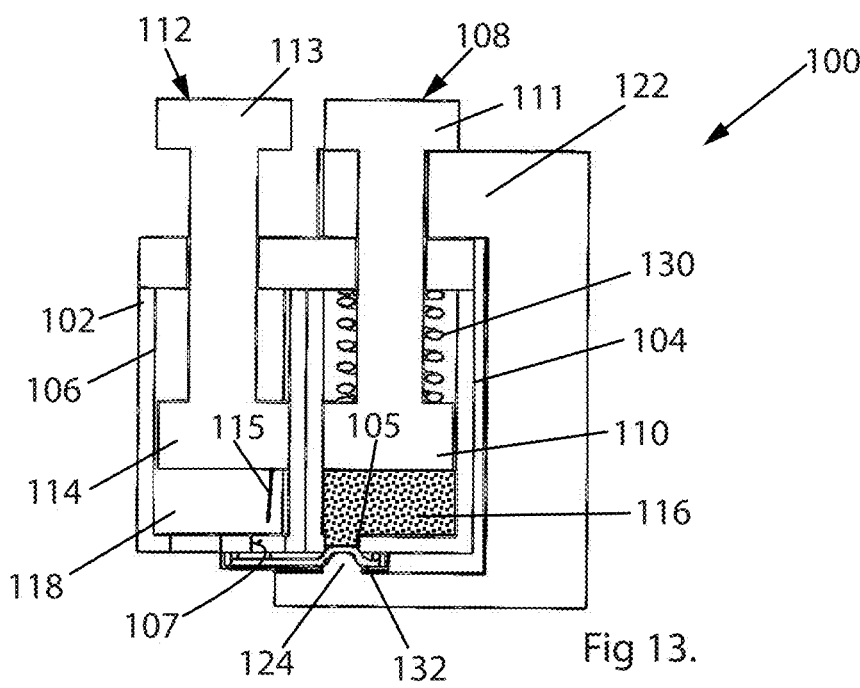
FIG. 13 is a diagrammatic representation of an example drug injection device for use with the example personal drug injection system shown in FIG. 8, 9 or 10, the drug injection device shown in a packaged, pre-activated configuration.
Figure 14:
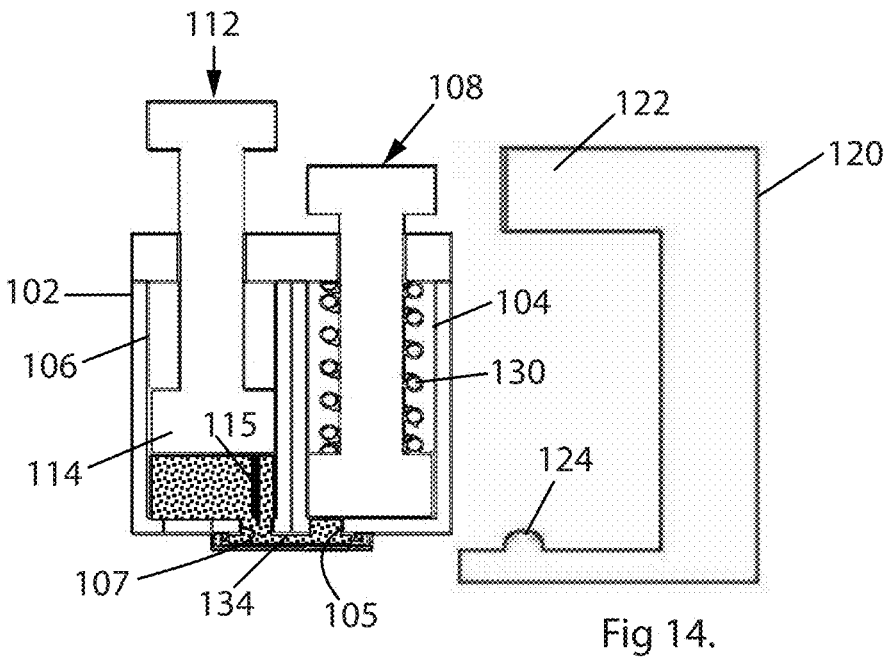
FIG. 14 is a diagrammatic representation of the drug injection device shown in FIG. 13, the drug injection device shown in an unpackaged, activated configuration prior to delivery of a drug.
Figure 15:
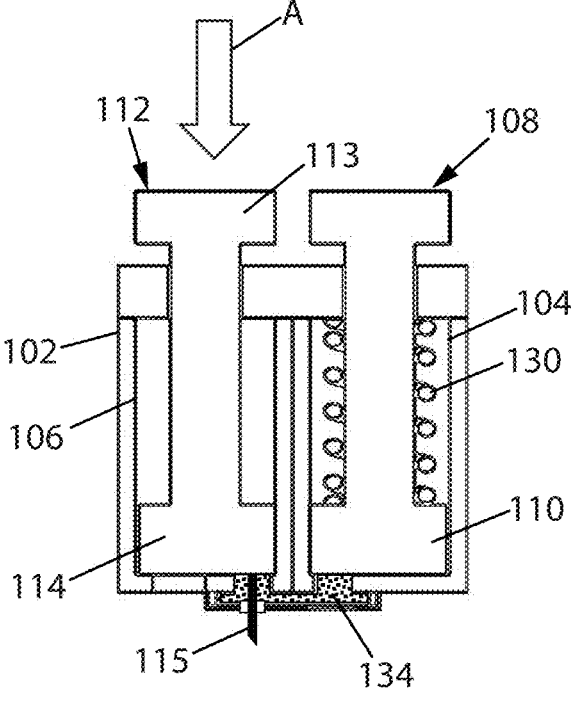
FIG. 15 is a diagrammatic representation of the drug injection device shown in FIGS. 13 and 14, the drug injection device shown in a used position after delivery of a drug.

In the present example, each injection site is arranged to receive and engage with a drug injection device, an example of which is shown in FIGS. 13 to 15 and described below.

In the present example, the defined pattern 82 of injection sites 84 is associated with a treatment process for treatment of migraine that uses the PREEMPT clinical program protocol, although it will be understood that any injection pattern relevant for a treatment process is envisaged.

Figure 9:
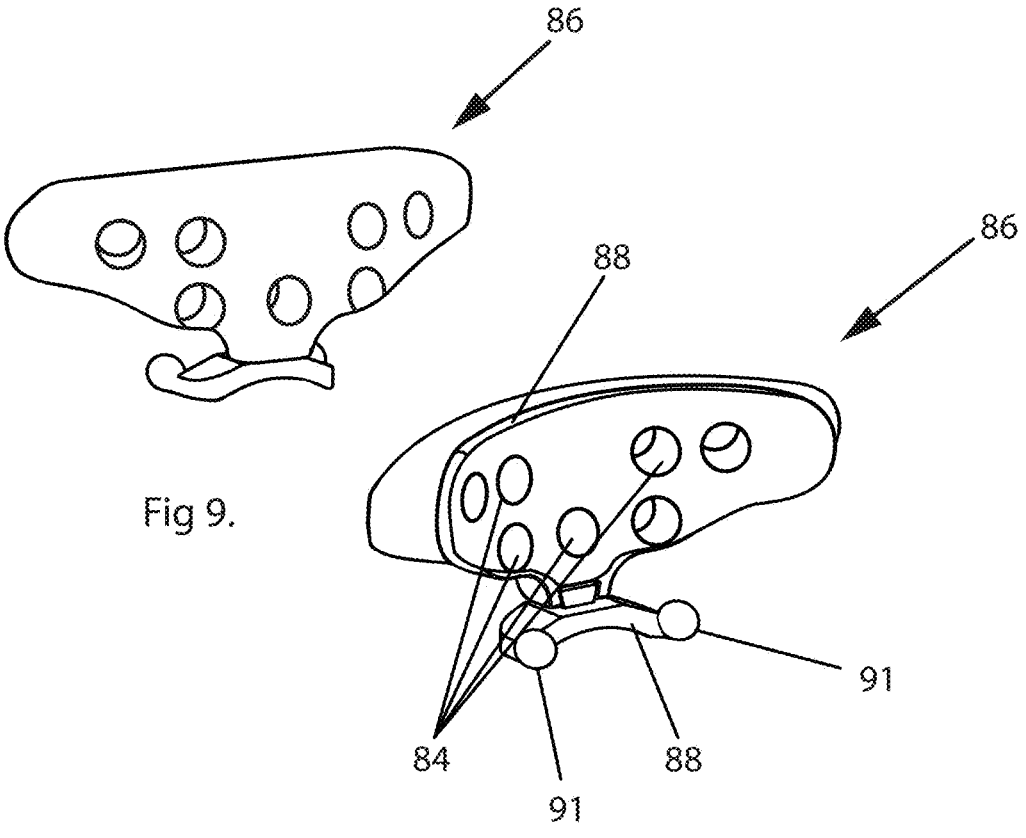
FIG. 9 is a representation of an example substantially rigid personal drug injection system.

In an example, as shown in FIG. 9, a mask device 86 is substantially rigid and for example produced using a 3D printer. Like and similar features are indicated with like reference numerals.

The rigid mask device 86 includes an alignment component 89 provided with 2 spaced pads 91, the alignment component 89 arranged such that the mask device 86 is correctly aligned with the person's face when the spaced pads 91 engage with the underside of a person's orbital ridges.

In this example, the rigid mask device 86 may also include a resilient layer 87 that may for example be formed of silicone material.

In an alternative example, as shown in FIG. 10, a mask device 90 is substantially flexible. Like and similar features are indicated with like reference numerals. The mask device 90 includes a first mask component 92 that forms a flexible skeleton defining the injection locations and a second flexible mask component 94, for example formed of silicone, to add structural integrity. With this arrangement an adhesive region 95 may be used since the flexibility of the mask device 90 enables the mask to be peeled from the person's face.

In this example, the mask device 90 is aligned manually with the person's face by aligning a lower flat surface 96 of the mask device 90 with an inner edge of an underside of the person's brow ridge, although it will be understood that any suitable alignment arrangement is envisaged.

In this example, the first component 92 is printed using a 3D printer and the second component 94 is formed from a silicone sheet. The first and second components 92, 94 are then disposed in a 3D printer mould and a third component overmoulded using 2-part curing silicone rubber.

Each drug injection mask device 80, 86, 90 may be provided with an integral drug reservoir such that the drug injection device is individually filled with a drug and individually activated.

The integral drug reservoir, including the surface of the reservoir that comes into contact with the drug, may comprise cyclic olefin copolymer (COC), cyclic olefin polymer, or a combination thereof. For example, the reservoir may have an inner surface containing the drug that is coated with COC, COP, or a combination thereof.

The substrate of a drug injection mask device, e.g., 80, 86, 90, may comprise, be composed of, consist of or, consist essentially of a polymer (e.g., acrylonitrile butadiene styrene (ABS), a polyalkylene, such as polyethylene, including high density polyethylene, polypropylene, a polyalkylene oxide, such as polyethylene glycol, polyvinyl chloride, a polyfluoroalkylene, a polyvinyl alcohol, an ester of polyvinyl alcohol, an acrylic, including a poly(alkylacrylate) such as poly(methylacrylate), a poly(alkylalkacrylate) such as poly(methylmethacrylate), a nylon, a polycarbonate, a polyethylene terephthalate, a polyethylene terephthalate glycol, a polystyrene, a fluoropolymer such as a polyflouroalkylene, a polyester, a polyimide, a thermomolded plastic, or a combination of co-polymer thereof), a metal (such as copper, iron, aluminum, cobalt, titanium, magnesium, manganese, etc., or an alloy thereof), wood, a wax, a cellulose material, a cellulose derivative, etc.

In some embodiments, the substrate of a drug injection mask device may have a thickness that is: about 8-30 mm, about 8-12 mm, about 12-16 mm, about 16-20 mm, about 20-25 mm, about 25-30 mm, about 8-10 mm, about 10-12 mm, about 12-14 mm, about 14-16 mm, about 16-18 mm, about 18-20 mm, about 20-22 mm, about 22-24 mm, about 24-26 mm, about 26-28 mm, or about 28-30 mm.

In some embodiments, a drug injection mask device may have 3-7 injection locations. Two of these injection locations, are referred to as a first outside injection location and a second outside injection location. The first outside injection location and the second outside injection location are located farthest in a horizontal direction, from the middle of the drug injection mask. The first outside injection location is illustrated, for the purpose of example only, by injection location 84A in FIG. 11. The second outside injection location is illustrated, for the purpose of example only, by injection location 84B in FIG. 11.

For a drug injection mask with 3-7 injection locations, two of these drug injection locations may be referred to as a first intermediate injection location and a second intermediate injection location. The first intermediate injection location and the second intermediate injection location are located closer, in a horizontal direction, to the middle of the drug injection mask than are the first outside injection location and the second outside drug injection location. The first intermediate injection location is illustrated, for the purpose of example only, by injection location 84C in FIG. 11. The second intermediate injection location is illustrated, for the purpose of example only, by injection location 84D in FIG. 11.

For a drug injection mask with 3-7 injection locations, one of these drug injection locations may be referred to as a middle injection location. The middle injection location is located at or near the horizontal middle of the drug injection mask, or may be positioned to be at or near the horizontal middle of a person's face. The middle injection location is illustrated, for the purpose of example only, by injection location 84E in FIG. 11.

In some embodiments, a drug injection mask may comprise a first outside injection location, a second outside injection location, a first intermediate injection location, a second intermediate injection location, and a middle injection location.

In some embodiments, a first outside injector is integrated into the substrate at the first outside injection location. In some embodiments, the first outside injector contains a drug.

In some embodiments, a second outside injector is integrated into the substrate at the second outside injection location. In some embodiments, the second outside injector contains a drug.

In some embodiments, a first intermediate injector is integrated into the substrate at the first intermediate injection location. In some embodiments, the first intermediate injector contains a drug.

In some embodiments, a second intermediate injector is integrated into the substrate at the second intermediate injection location. In some embodiments, the second intermediate injector contains a drug.

In some embodiments, a middle injector is integrated into the substrate at the middle injection location. In some embodiments, the middle injector contains a drug.

In some embodiments, the first outside injector, the second outside injector, the first intermediate injector, the second intermediate injector, and the middle injector contain a drug.

The first outside injector, the second outside injector, the first intermediate injector, the second intermediate injector, and the middle injector may be any suitable injectors. The injectors depicted in FIGS. 13-15 are non-limiting examples of suitable injectors.

Drug Injection Mask Type A

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type A.

In drug injection mask type A, the horizontal distance between the first outside injection location and the second outside injection location may be about 50-60 mm, about 50-53 mm, about 53-56 mm, about 56-60 mm, or about 54 mm.

In some embodiments of drug injection mask type A, the horizontal distance between the first outside injection location and the first intermediate injection location may be about 12-15 mm, about 13-14 mm, or about 13.3-13.7 mm. In some embodiments of drug injection mask type A, the horizontal distance between the second outside injection location and the second intermediate injection location may be about 12-15 mm, about 13-14 mm, or about 13.3-13.7 mm.

In some embodiments of drug injection mask type A, the horizontal distance between the first intermediate injection location and the middle injection location may be about 12-15 mm, about 13-14 mm, or about 13.3-13.7 mm. In some embodiments of drug injection mask type A, the horizontal distance between the second intermediate injection location and the middle injection location may be about 12-15 mm, about 13-14 mm, or about 13.3-13.7 mm.

In some embodiments of drug injection mask type A, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type A, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type A, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type A, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type A, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type A, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type B

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type B.

In drug injection mask type B, the horizontal distance between the first outside injection location and the second outside injection location may be about 55-65 mm, about 55-58 mm, about 58-61 mm, about 61-65 mm, or about 59 mm.

In some embodiments of drug injection mask type B, the horizontal distance between the first outside injection location and the first intermediate injection location may be about 13-16 mm, about 14-15 mm, or about 14.5-15 mm. In some embodiments of drug injection mask type B, the horizontal distance between the second outside injection location and the second intermediate injection location may be about 13-16 mm, about 14-15 mm, or about 14.5-15 mm.

In some embodiments of drug injection mask type B, the horizontal distance between the first intermediate injection location and the middle injection location may be about 13-16 mm, about 14-15 mm, or about 14.5-15 mm. In some embodiments of drug injection mask type B, the horizontal distance between the second intermediate injection location and the middle injection location may be about 13-16 mm, about 14-15 mm, or about 14.5-15 mm.

In some embodiments of drug injection mask type B, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type B, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type B, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type B, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type B, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type B, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type C

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type C.

In drug injection mask type C, the horizontal distance between the first outside injection location and the second outside injection location may be about 58-68 mm, about 58-62 mm, about 62-64 mm, about 64-68 mm, or about 63 mm.

In some embodiments of drug injection mask type C, the horizontal distance between the first outside injection location and the first intermediate injection location may be about 14-17 mm, about 15-16 mm, or about 15.5-16 mm. In some embodiments of drug injection mask type C, the horizontal distance between the second outside injection location and the second intermediate injection location may be about 14-17 mm, about 15-16 mm, or about 15.5-16 mm.

In some embodiments of drug injection mask type C, the horizontal distance between the first intermediate injection location and the middle injection location may be about 14-17 mm, about 15-16 mm, or about 15.5-16 mm. In some embodiments of drug injection mask type C, the horizontal distance between the second intermediate injection location and the middle injection location may be about 14-17 mm, about 15-16 mm, or about 15.5-16 mm.

In some embodiments of drug injection mask type C, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type C, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type C, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type C, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type C, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type C, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type D

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type D.

In drug injection mask type D, the horizontal distance between the first outside injection location and the second outside injection location may be about 62-72 mm, about 62-66 mm, about 66-68 mm, about 68-72 mm, or about 67 mm.

In some embodiments of drug injection mask type D, the horizontal distance between the first outside injection location and the first intermediate injection location may be about 15-18 mm, about 16-17 mm, or about 16.5-17 mm. In some embodiments of drug injection mask type D, the horizontal distance between the second outside injection location and the second intermediate injection location may be about 15-18 mm, about 16-17 mm, or about 16.5-17 mm.

In some embodiments of drug injection mask type D, the horizontal distance between the first intermediate injection location and the middle injection location may be about 15-18 mm, about 16-17 mm, or about 16.5-17 mm. In some embodiments of drug injection mask type D, the horizontal distance between the second intermediate injection location and the middle injection location may be about 15-18 mm, about 16-17 mm, or about 16.5-17 mm.

In some embodiments of drug injection mask type D, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type D, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type D, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type D, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type D, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type D, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type E

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type E.

In drug injection mask type E, the horizontal distance between the first outside injection location and the second outside injection location may be about 68-78 mm, about 68-72 mm, about 72-74 mm, about 74-78 mm, or about 73-74 mm.

In some embodiments of drug injection mask type E, the horizontal distance between the first outside injection location and the first intermediate injection location may be about 16-20 mm, about 18-19 mm, or about 18-18.5 mm. In some embodiments of drug injection mask type E, the horizontal distance between the second outside injection location and the second intermediate injection location may be about 16-20 mm, about 18-19 mm, or about 18-18.5 mm.

In some embodiments of drug injection mask type E, the horizontal distance between the first intermediate injection location and the middle injection location may be about 16-20 mm, about 18-19 mm, or about 18-18.5 mm. In some embodiments of drug injection mask type E, the horizontal distance between the second intermediate injection location and the middle injection location may be about 16-20 mm, about 18-19 mm, or about 18-18.5 mm.

In some embodiments of drug injection mask type E, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type E, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type E, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type E, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type E, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type E, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type F

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type F.

In some embodiments of drug injection mask type F, the horizontal distance between the first outside injection location and the middle injection location may be about 28-32 mm, about 29-30 mm, or about 29.5 mm. In some embodiments of drug injection mask type F, the horizontal distance between the second outside injection location and the middle injection location may be about 28-32 mm, about 29-30 mm, or about 29.5 mm.

In some embodiments of drug injection mask type F, the horizontal distance between the first intermediate injection location and the middle injection location may be about 10-14 mm, about 11-12 mm, or about 11.5-12 mm. In some embodiments of drug injection mask type F, the horizontal distance between the second intermediate injection location and the middle injection location may be about 10-14 mm, about 11-12 mm, or about 11.5-12 mm.

In some embodiments of drug injection mask type F, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type F, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type F, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type F, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type F, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type F, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type G

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type G.

In some embodiments of drug injection mask type G, the horizontal distance between the first outside injection location and the middle injection location may be about 30-34 mm, about 31-32 mm, or about 31.5 mm. In some embodiments of drug injection mask type G, the horizontal distance between the second outside injection location and the middle injection location may be about 30-34 mm, about 31-32 mm, or about 31.5 mm.

In some embodiments of drug injection mask type G, the horizontal distance between the first intermediate injection location and the middle injection location may be about 14-17 mm, about 14.5-15.5 mm, or about 15 mm. In some embodiments of drug injection mask type G, the horizontal distance between the second intermediate injection location and the middle injection location may be about 14-17 mm, about 14.5-15.5 mm, or about 15 mm.

In some embodiments of drug injection mask type G, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type G, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type G, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type G, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type G, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type G, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

Drug Injection Mask Type H

Some drug injection masks comprising a first outside injection location (optionally having a first outside injector integrated into the substrate at this location), a second outside injection location (optionally having a second outside injector integrated into the substrate at this location), a first intermediate injection location (optionally having a first intermediate injector integrated into the substrate at this location), a second intermediate injection location (optionally having a second intermediate injector integrated into the substrate at this location), and a middle injection location (optionally having a middle injector integrated into the substrate at this location), may be referred to for convenience as drug injection mask type H.

In some embodiments of drug injection mask type H, the horizontal distance between the first outside injection location and the middle injection location may be about 32-36 mm, about 33-34 mm, or about 33.5 mm. In some embodiments of drug injection mask type H, the horizontal distance between the second outside injection location and the middle injection location may be about 30-34 mm, about 31-32 mm, or about 31.5 mm.

In some embodiments of drug injection mask type H, the horizontal distance between the first intermediate injection location and the middle injection location may be about 16-20 mm, about 17-19 mm, or about 18 mm. In some embodiments of drug injection mask type D, the horizontal distance between the second intermediate injection location and the middle injection location may be about 16-20 mm, about 17-19 mm, or about 18 mm.

In some embodiments of drug injection mask type H, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the first intermediate injection location.

In some embodiments of drug injection mask type H, the vertical position of the first outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type H, the vertical position of the first intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type H, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the second intermediate injection location.

In some embodiments of drug injection mask type H, the vertical position of the second outside injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In some embodiments of drug injection mask type H, the vertical position of the second intermediate injection location may be within 30 mm or within 20 mm from, such as about 2-7 mm, about 7-12 mm, about 12-17 mm, about 2-4 mm, about 4-6 mm, about 6-9 mm, about 9-12 mm, about 12-14 mm, about 14-16 mm, or about 14-17 mm from the vertical position of the middle injection location.

In an alternative arrangement, as shown in FIG. 12, the drug injection devices may be connected to a common drug source 97 using a common injection arrangement 98. Like and similar features are indicated with like reference numerals. With this arrangement, a drug is drawn from the common drug source 97 and supplied to multiple drug injection devices 100 as part of the drug injection process.

In an example that uses a neurotoxin such as botulinum toxin, the toxin may be in any suitable format, including lyophilised, freeze dried or in-solution.

The drug injection devices may be of a type that facilitates reconstitution of a drug in situ or that houses a drug that does not require mixing with any other component prior to injection, for example a liquid in-solution formulation such as Alluzience®.

Referring to FIG. 13, an example drug injection device 100 is shown.

In the present example, the drug injection device 100 is for use with a drug having 2 components that are held separately and brought together to form an injectable drug shortly prior to injection into a person. However, it will be understood that the drug injection device may alternatively be of a type arranged to hold a single component drug that does not require mixing prior to injection.

The drug injection device 100 includes a housing 102 that defines a first chamber 104 having a first chamber opening 105 and a second chamber 106 having a second chamber opening 107.

A first plunger 108 is slidably received in the first chamber 104 and includes a first plunger head 110 and a first plunger end 111. The first plunger 108 is biased to move inwardly of the first chamber 104, in this example using a biasing device in the form of a coil spring 130. A second plunger 112 is slidably received in the second chamber 106 and includes a second plunger head 114 and a second plunger end 113. A needle 115 is mounted on and extends away from the second plunger head 114.

A first substance 116 is disposed in the first chamber 104 and a second substance 118 is disposed in the second chamber 106, and the device 100 is arranged to prevent contact between the first and second substances 116, 118 until activation of the device 100 by a user. In the present example, activation of the device 100 is achieved by providing a removable packaging member 120 that has a plunger stop portion 122 disposed between the first plunger end 111 and the housing 102 to prevent movement of the first plunger 108 inwardly of the first chamber 104 under action of the coil spring 130. A flexible membrane 132 extends across the first chamber opening 105, and the packaging member 120 includes an outlet seal portion 124 that acts towards the first chamber opening 105 against the flexible membrane 132 to seal the first chamber opening 105 and prevent egress of the first substance 116 from the first chamber 104. In this example, the outlet seal portion 124 is a nipple member that extends in the first chamber opening 105 and urges the flexible membrane against the first chamber opening 105 when the packaging member 120 is engaged with the housing 102.

When the packaging member 120 is removed by a person, as shown in FIG. 14, the outlet seal portion 124 is able to move away from the first chamber opening 105 to define a fluid path 134 between the first chamber opening 105 and the second chamber opening 107. In addition, in the absence of the plunger stop portion 122 between the housing 102 and the first plunger end 111, the first plunger 108 is caused to move inwardly of the first chamber 104 by the coil spring 130, which causes the first substance to move from the first chamber 104 through the fluid path 134 into the second chamber 106, thereby mixing with the second substance 118.

In the present example, the first substance is saline solution and the second substance is a mixture of botulinum toxin powder, sodium chloride and albumin, although it will be understood that any suitable first and second substances are envisaged depending on the proposed treatment process.

In the present example, the injection device 100 is arranged to deliver about 0.1 mL of saline and about 0.07 mg of botulinum toxin powder, sodium chloride and albumin mixture that may comprise 0.045 mg of sodium chloride, 0.025 mg of albumin and 0.25 ng of botulinum toxin.

As shown in FIG. 15, after the first and second substances have mixed together to form an injectable drug, the drug is dispensed by application of a manual force to the second plunger 112, as indicated by arrow A. This action causes the second plunger 112 to move inwardly of the second chamber 106 and the drug to be injected into a person through the needle 115.

With respect to any portion of an injection device that comes into contact with a drug, any silicone component comprise poly(ethene-co-tetrafluoroethene) (ETFE) coated bromobutyl silicone. The ETFE coating may help to stop oxygen radicals from penetrating the silicone over time and denaturing the toxin.

For example, any plunger described herein, such as first plunger 108 and second plunger 112, may comprise ETFE coated bromobutyl silicone.

In another example, any fluid path between two drug-containing chambers, e.g., fluid path 134 between first chamber 104 and second chamber 106, may be contained within walls comprising ETFE coated bromobutyl silicone.

Figure 16:
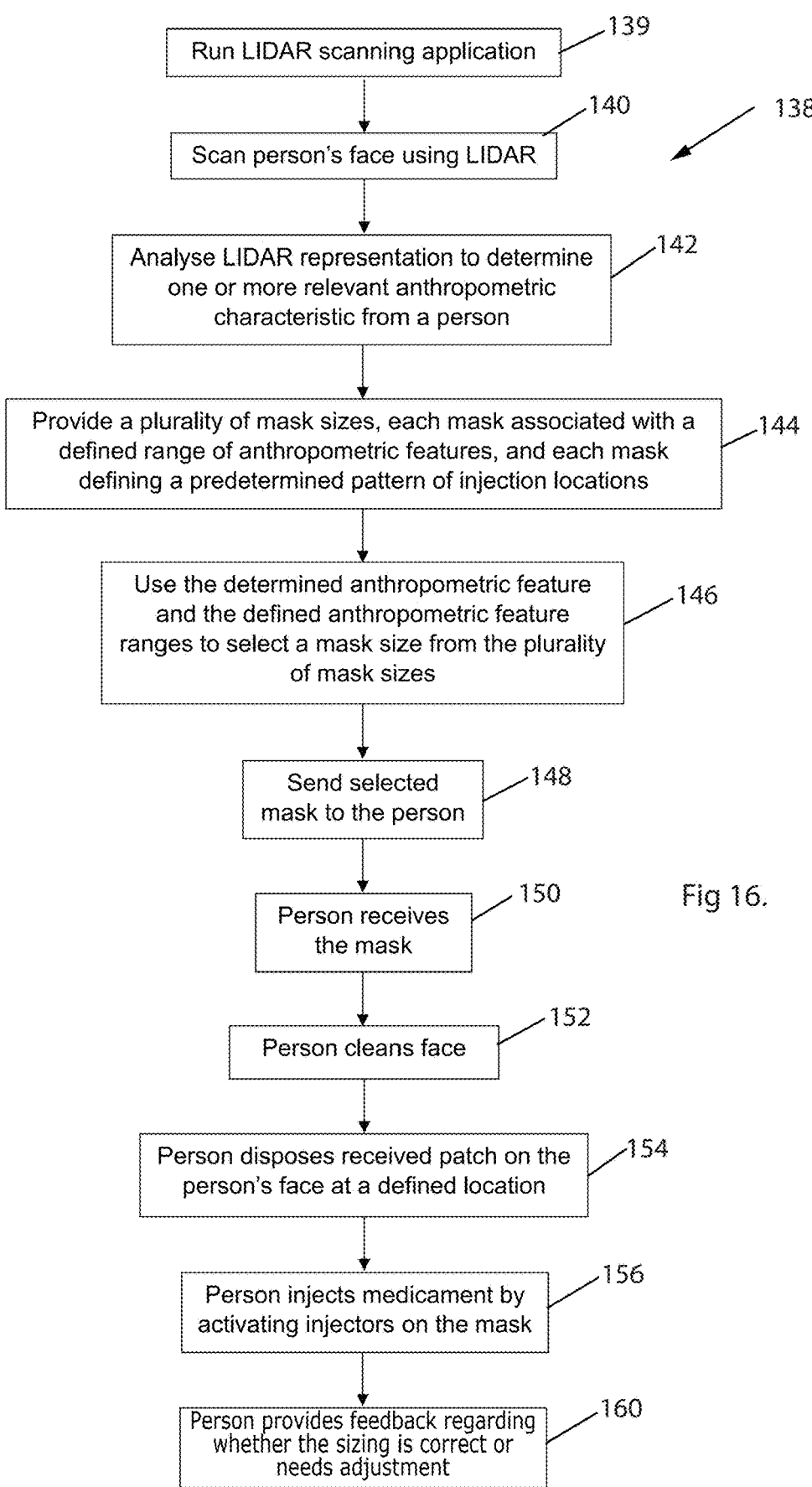
FIG. 16 is a flow diagram illustrating a method of providing an embodiment of a personal drug injection.

FIG. 16 shows a flow diagram 138 illustrating steps 139 to 156 of an example method of providing a drug injection system to a person.

The method involves first determining one or more relevant anthropometric characteristics from a person, in this example intercanthal separation that is used to determine locations of the person's inner orbital ridge edges, as indicated at steps 139 to 142.

In this example, the intercanthal separation distance is determined using a LIDAR scanner provided on a smartphone and an associated software application implemented on the smartphone. The LIDAR scanner produces a point cloud representation of the person's face that is then used by a software application on the smartphone to determine the intercanthal separation distance.

Based on the determined intercanthal separation, a mask device 80, 86, 90 is selected that has an injection pattern appropriate for the determined intercanthal separation, as indicated at steps 144 and 146. The selected mask device 80, 86, 90 is then provided to the person, for example by mail, as indicated at steps 148 and 150. After cleaning/disinfecting the person's face, the mask 80, 86, 90 is disposed on the person's face and aligned relative to the face, for example by aligning the mask 80 with the person's inner orbital ridge edges, as indicated at steps 152 and 154. The person then uses the injection devices on the mask to inject the drug at the required injection sites defined by the injection pattern 82 of the mask 80, as indicated at step 156. The person then provides feedback regarding whether the sizing of mask 80 is correct or needs adjustment, as indicated at step 160. This feedback is used to adjust the algorithm.

The following documents are incorporated by reference in their entireties: Australian Pat. App. No. AU2024900090, filed on Jan. 12, 2024, and U.S. Prov. Pat. App. No. 63/688,241, filed on Aug. 28, 2024.

In the claims that follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

It is to be understood that, if any prior art publication is referred to herein, such reference does not constitute an admission that the publication forms a part of the common general knowledge in the art, in the United States or any other country.

Modifications and variations as would be apparent to a skilled addressee are deemed to be within the scope of the present invention.

The invention claimed is:

1. A drug injection device including a first chamber containing a first substance and a second chamber containing a second substance, wherein fluid communication between the first chamber and the second chamber is prevented when a removable packaging member is attached to the drug injection device and fluid communication between the first chamber and the second chamber is enabled when the removable packaging member is removed from the drug injection device, wherein the first chamber includes a first chamber opening, the second chamber includes a second chamber opening, and the drug injection device includes a flexible membrane disposed over at least one of the first chamber opening and the second chamber openings, wherein the removable packaging member directly engages with: the flexible membrane and the first chamber opening, the flexible membrane and second chamber opening, or the flexible membrane and both the first chamber opening and the second chamber opening, to prevent fluid communication between the first chamber and the second chamber when the removable packaging member is attached to the drug injection device.

2. The drug injection device of claim 1, wherein at least one of the first chamber and the second chamber includes a first plunger and a biasing device arranged to bias the first plunger inwardly of the associated first or second chamber, wherein inward movement of the first plunger by the biasing device is prevented when the packaging member is attached to the drug injection device, and the inward movement of the first plunger by the biasing device is enabled when the packaging member is removed from the drug injection device, such that removal of the packaging member causes the first substance and the second substance to mix.

3. The drug injection device of claim 2, wherein the biasing device is a spring.

4. The drug injection device of claim 2, wherein the other of the first chamber and the second chamber includes a second plunger and a needle, wherein inward movement of the second plunger after mixing of the first substance and the second substance causes dispensation of the mixed substances through the needle.

5. A method of providing a personal drug injection system, the method comprising:

using a physical instrument to obtain at least one anthropometric characteristic value by interaction between the physical instrument and a part of a person's body that is intended to receive an injectable drug;

providing at least 3 personal drug injection system types, wherein each of the at least 3 personal drug injection system types is a drug injection device of claim 1, wherein each personal drug injection system type is configured to fit with the part of the person's body, wherein the at least 3 personal drug injection system types include:

a first personal drug injection system type having a first drug injection location set that includes at least one defined drug injection location corresponding to a location of a drug injection site on the part of the person's body when the first personal drug injection system type is disposed on the part of the person's body, the first personal drug injection system type associated with a first defined range of anthropometric characteristic values;

a second personal drug injection system type having a second drug injection location set that includes at least one defined drug injection location corresponding to a location of a drug injection site on the part of the person's body when the second personal drug injection system type is disposed on the part of the person's body, the second drug injection location set being different from the first drug injection location set of the first personal drug injection system type, and the second personal drug injection system type associated with a second defined range of anthropometric characteristic values that is different to the first defined range of anthropometric characteristic values; and a third personal drug injection system type having a third drug injection location set that includes at least one defined drug injection location corresponding to a location of a drug injection site on the part of the person's body when the third personal drug injection system type is disposed on the part of the person's body, the third drug injection location set being different from both the first drug injection location set of the first personal drug injection system type and the second drug injection location set of the second personal drug injection system type, and the third personal drug injection system type is associated with a third defined range of anthropometric characteristic values that is different from both the first defined range of anthropometric characteristic values and the second defined range of anthropometric characteristic values;

selecting one of the at least 3 personal drug injection system types by determining which of the first defined range of anthropometric characteristic values, the second defined range of anthropometric characteristic values, or the third defined range of anthropometric characteristic values includes the anthropometric characteristic value obtained from the person; and providing the person with the selected personal drug injection system type.

6. The method of claim 5, wherein the at least one anthropometric characteristic value includes intercanthal separation distance.

7. The method of claim 6, wherein the at least one anthropometric characteristic value includes distance between medial edges of the person's orbital ridges.

8. The method of claim 5, comprising:

using the physical instrument to determine at least one first anthropometric characteristic value by interaction between the physical instrument and the part of the person's body;

using the first anthropometric characteristic value to determine at least one second anthropometric characteristic value; and using the second anthropometric characteristic value and the first anthropometric characteristic value to select one of the personal drug injection system types from the at least 3 personal drug injection system types.

9. The method of claim 5, comprising determining the at least one anthropometric characteristic value by obtaining a 3D representation of at least a portion of a person's body by interaction between the physical instrument and the portion of the person's body.

10. The method of claim 9, wherein the 3D representation is obtained by interaction between a LIDAR scanner and the portion of the person's body and the method comprises analysing the 3D representation to determine the at least one anthropometric characteristic value.

11. The method of claim 5, comprising determining the anthropometric characteristic value by capturing an image of at least a portion of the person's body and analysing the image to determine the at least one anthropometric characteristic value.

12. The method of claim 5, comprising determining the anthropometric characteristic value by using the physical instrument to directly measure the at least one anthropometric characteristic value.

13. The method of claim 5, comprising using machine learning to predict the at least one anthropometric characteristic value and/or to select a personal drug injection system type from the at least 3 personal drug injection system types.

14. The method of claim 13, wherein using machine learning includes using at least one convolutional neural network (CNN) trained using multiple body part representations and data indicative of at least one anthropometric characteristic value associated with each body part representation.

15. The method of claim 5, wherein at least one personal drug injection system is at least partially rigid.

16. The method of claim 5, wherein at least one personal drug injection system is at least partially flexible.

17. The method of claim 5, comprising providing at least one personal drug injection system type with at least one fixed drug injection device.

18. The method of claim 5, comprising providing at least one personal drug injection system type with at least one removable and attachable drug injection device.

19. The method of claim 5, comprising providing at least one personal drug injection system type with at least one alignment component arranged to facilitate correct alignment of the personal drug injection system type with the person's body part.

20. The method of claim 19, wherein the alignment component is arranged to engage with a defined feature of the person's body part such that the personal drug injection system type is correctly aligned with the person's body part when the alignment component engages with the defined feature of the person's body part.

21. The method of claim 20, wherein the defined feature is an underside of a person's orbital ridges.

22. The method of claim 19, wherein the alignment component comprises a visual feature of the personal drug injection system type that is usable to align the personal drug injection system type with the person's body part by visually aligning the visual feature with a defined feature of the person's body part.

23. The method of claim 22, wherein the visual feature includes a lower flat surface of the personal drug injection system type and the defined feature includes an inner edge of an underside of the person's brow ridge.

24. The method of claim 5, the part of the person's body may include at least a portion of a face of the person.

25. The method of claim 24, wherein the personal drug injection system includes a mask device that covers at least part of the person's face.

26. The method of claim 5, wherein the injectable drug includes a neuromodulator.

27. The method of claim 26, wherein the neuromodulator includes botulinum toxin.

28. The method of claim 27, wherein the neuromodulator is a synthetically derived analogue of botulinum toxin.

* * * * *